United States Patent [19]

Fost et al.

[11] Patent Number: 5,286,719
[45] Date of Patent: Feb. 15, 1994

[54] PHOSPHOLIPID VIRUCIDAL COMPOSITIONS

[75] Inventors: Dennis L. Fost, Ridgewood; Joseph A. Komor, Ramsey, both of N.J.

[73] Assignee: Mona Industries, Inc., Paterson, N.J.

[21] Appl. No.: 901,204

[22] Filed: Jun. 19, 1992

Related U.S. Application Data

[63] Continuation-in-part of Ser. No. 784,154, Oct. 28, 1991.

[51] Int. Cl.$^5$ .............................. A61K 31/685
[52] U.S. Cl. ................... 514/114; 514/119
[58] Field of Search ................ 514/114, 119

[56] References Cited

U.S. PATENT DOCUMENTS

| | | | |
|---|---|---|---|
| 3,228,829 | 1/1966 | Wolf et al. | 167/33 |
| 3,304,349 | 2/1967 | Kwan-Ting Shen | 260/920 |
| 3,830,913 | 8/1974 | Harich | 424/195 |
| 4,202,882 | 5/1980 | Schwartz | 424/76 |
| 4,209,449 | 6/1980 | Mayhew et al. | 260/403 |
| 4,215,064 | 7/1980 | Lindemann et al. | 260/403 |
| 4,233,192 | 11/1980 | Lindemann et al. | 252/545 |
| 4,243,602 | 1/1980 | O'Lenick, Jr. et al. | 260/403 |
| 4,261,911 | 4/1981 | Lindemann et al. | 260/403 |
| 4,283,542 | 8/1981 | O'Lenick, Jr. et al. | 548/112 |
| 4,308,637 | 4/1983 | Lindemann et al. | 548/112 |
| 4,323,602 | 4/1982 | Parker | 427/298 |
| 4,336,385 | 6/1982 | Mayhew et al. | 548/112 |
| 4,336,386 | 6/1982 | O'Lenick, Jr. et al. | 548/112 |
| 4,503,002 | 3/1985 | Mayhew et al. | 260/945 |
| 4,844,891 | 7/1989 | Rosen et al. | 424/76.4 |

OTHER PUBLICATIONS

Mona Industries, Technical Bulletin, No. 905-1a, Apr. 1983.
Mona Industries, Technical Bulletin, No. 905d, Dec. 1989.

*Primary Examiner*—Mary C. Lee
*Assistant Examiner*—Michael G. Ambrose
*Attorney, Agent, or Firm*—Franklyn Schoenberg

[57] ABSTRACT

There is provided a method for protecting substrates subject to contact by infectious viral organisms by treating such substrates with virucidally effective amount of a composition containing a synthetic phospholipid of the formula:

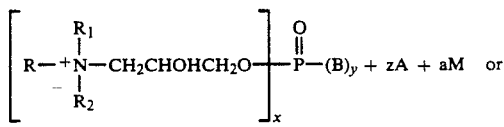

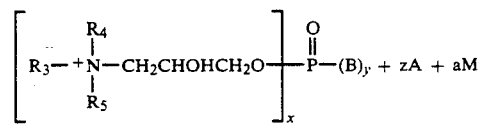

wherein:
x is 1 to 3 or mixtures thereof;
x+y=3;
z=x;
a=0 to 2;
B=O$^-$ or OM;
A is an Anion;
M is a Cation;
R$_3$ is an amidoamine moiety of the formula:

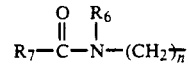

wherein:
n is an integer from about 2 to 6. R$_4$, R$_5$, R$_6$, and R$_7$ are as defined in the specification.

3 Claims, No Drawings

PHOSPHOLIPID VIRUCIDAL COMPOSITIONS

REFERENCE TO RELATED APPLICATION

This application is a continuation-in-part of application Ser. No. 784,154, filed Oct. 28, 1991.

FIELD OF THE INVENTION

The present invention relates to novel antimicrobial compositions and, more particularly, to a class of compounds having specific quaternized amine compounds linked to specific phosphate esters which exhibit broad spectrum antimicrobial activity and also virucidal activity referred to hereinafter as "antimicrobial/virucidal phospholipids". The phospholipids of the invention are well tolerated by human tissue making them suitable for use in the preparation of personal care, household cleaning, germicidal disinfectant and cleaning and like products which exhibit enhanced antimicrobial and virucidal characteristics.

BACKGROUND OF THE INVENTION

Phosphate ester and quaternary amine compounds are well known and have been widely used for many years for a variety of applications including those requiring surfactant properties. Known phosphate esters do not generally exhibit any antimicrobial characteristics, and while quaternary amine compounds are known in general to exhibit antimicrobial activity, such compounds are extremely irritating and thus have limited usefulness in personal care and cosmetic products. More recently, various betaine-type derivatives having, in general, quaternized alkyl amine groups and at least one phosphorus-containing anion in the molecule referred to hereinafter as "synthetic phospholipids", have been disclosed and suggested as, for example, in U.S. Pat. Nos. 4,215,064, 4,233,192 and 4,380,637 to Lindemann et al., U.S. Pat. Nos. 4,209,449, 4,336,385 and 4,503,002 to Mayhew et al., and U.S. Pat. Nos. 4,243,602, 4,283,542 and 4,336,386 to O'Lenick et al. These synthetic phospholipids are suggested as exhibiting an outstanding combination of surfactant characteristics as well as being well tolerated by human tissue, i.e., they exhibit exceptionally low ocular irritation and oral toxicity. While these known phospholipids have been found useful as surfactants in a variety of personal care, household cleaning and the like products, such products also require the incorporation of antimicrobial preservatives to inhibit microbial spoilage and increase shelf life, and there is no suggestion that any of these compounds exhibit virucidal activity.

SUMMARY OF THE INVENTION

In accordance with the present invention there has now been discovered novel phospholipid agents which surprisingly exhibit both excellent broad spectrum antibacterial and antifungal activity suitable for use as preservative and/or disinfectant agents in a variety of personal care compositions, household cleaning formulations and the like. These agents have also been found to possess potent virucidal activity making them particularly useful as a disinfectant, and for immobilizing and/or killing a variety of infectious viruses. The novel antimicrobial agents of the invention, which also exhibit virucidal properties, comprise particular synthetic phospholipid compounds that may be represented by the following general formula:

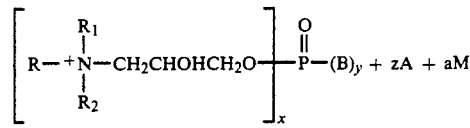

wherein:
x = 1 to 3 or mixtures thereof;
x + y = 3;
z = x
a = 0 to 2;
B = O$^-$ or OM;
A = Anion;
M is a cation;
R, $R_1$ and $R_2$ are the same or different and are alkyl, substituted alkyl, alkyl aryl or alkenyl groups of up to 16 carbon atoms with the proviso that the total carbon atoms in R + $R_1$ + $R_2$ is between 10 and 24.

It has been discovered that the particular synthetic antimicrobial phospholipids of the invention not only surprisingly and unexpectedly exhibit both broad spectrum bactericidal and fungicidal activity suitable for use as preservative and/or disinfectant agents in personal care and household products, but such phospholipid compositions surprisingly also exhibit potent virucidal activity making them useful, for example, as a disinfectant in hospitals and the like. Moreover, such agents are extremely well tolerated by human tissue, i.e., they exhibit exceptionally low ocular and skin irritation and oral toxicity, and can be used in product formulations containing nonionic, anionic, amphoteric and/or cationic components without significant inhibition or reduction of the required antimicrobial and/or virucidal activity. Thus, such agents may be formulated into a wide range of end products among which are germicidal cleaning compositions for hospitals and the like. The antimicrobial agents of the invention may also be used in combination with other known antimicrobial agents, when desired for particular applications, to enhance the antimicrobial and virucidal efficacy thereof.

In another aspect of the invention, there is provided a method of inhibiting the growth of microorganisms in personal care, household cleaning and the like products which comprises incorporating in a personal care or household cleaning formulation an antimicrobially effective amount of an antimicrobial phospholipid compound of the general formula:

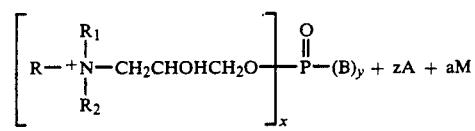

wherein:
x = 1 to 3 or mixtures thereof;
x + y = 3;
z = x;
a = 0 to 2;
B = O$^-$ or OM;
A = Anion;
M is a cation;
R, $R_1$ and $R_2$ are the same or different and are alkyl, substituted alkyl, alkyl aryl or alkenyl groups of up to 16 carbon atoms with the proviso that the total carbon atoms in R + $R_1$ + $R_2$ is between 10 and 24.

In a still further aspect of the present invention, there is provided a personal care composition or a household cleaning composition which comprises a surface active agent and an antimicrobial effective amount of an antimicrobial phospholipid compound component of the general formula:

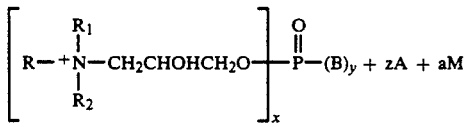

wherein:
x = 1 to 3 or mixtures thereof;
x + y = 3;
z = x;
a = 0 to 2;
B = O⁻ or OM;
A = Anion;
M is a cation;
R, R₂ and R₂ are the same or different and are alkyl, substituted alkyl, alkyl aryl or alkenyl groups of up to 16 carbon atoms with the proviso that the total carbon atoms in R+R₁+R₂ is between 10 and 24.

In yet another aspect of the invention there are provided compositions for use in the killing and/or immobilizing a variety of infectious viral organisms including disinfectant protection which comprises a virucidally effective amount of a antimicrobial/virucidal phospholipid agent of the general formula:

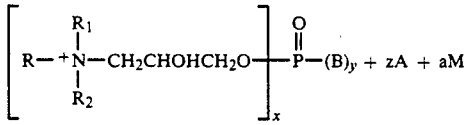

wherein:
x = 1 to 3 or mixtures thereof;
x + y = 3;
z = x;
a = 0 to 2;
B = O⁻ or OM;
A = Anion;
M is a cation;
R, R₁ and R₂ are the same or different and are alkyl, substituted alkyl, alkyl aryl or alkenyl groups of up to 16 carbon atoms with the proviso that the total carbon atoms in R+R₁+R₂ is between 10 and 24; or a virucidal agent of the general formula:

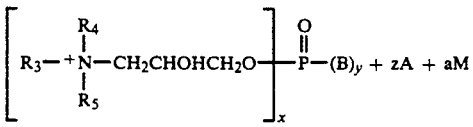

wherein:
x is as hereinabove defined;
x + y = 3;
z = x;
a = 0 to 2;
B = O⁻ or OM;
A is on Anion;
M is a Cation;

$R_3$ is an amidoamine moiety of the formula:

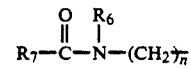

wherein:
$R_7$ is alkyl, alkenyl, alkoxy or hydroxyalkyl of from 5 to 21 carbon atoms each, or aryl or alkaryl of up to 20 carbon atoms;
$R_6$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkylene of up to 10 carbon atoms;
$R_4$ and $R_5$, which may be the same or different, are selected from alkyl, hydroxyalkyl, carboxyalkyl of up to 6 carbon atoms in each alkyl moiety, and polyoxyalkylene of up to 10 carbon atoms; in addition $R_4$ and $R_5$ taken together with the nitrogen to which they are attached may represent an N-heterocycle; and
n is an integer from 2 to 6.

As used herein the phrases "antimicrobial" and "inhibiting microbial growth" describes the killing of, as well as the inhibition or control of the growth of bacteria (gram positive and gram negative), fungi, yeasts and molds.

As used herein the phrase "virucidal" describes the killing of as well as the immobilization of infectious virus organisms.

DETAILED DESCRIPTION OF THE INVENTION

The present invention is directed to novel phospholipid agents which surprisingly and unexpectedly exhibit excellent broad spectrum bactericidal and fungicidal activity and effectiveness, effectively inhibit the growth of a variety of bacteria, yeasts, and molds as well as possessing potent virucidal killing and/or immobilizing activity for a variety of infectious viruses. Moreover, such active agents may be used in combination with or in the presence of anionic, nonionic, amphoteric and/or cationic surfactants without inhibition of the antimicrobial and virucidal efficacy thereof and are virtually non-irritating to the skin and eyes; thus, such antimicrobial agents may be used in diverse formulations and applications.

The novel antimicrobial/virucidal agents of the present invention comprise a class of synthetic phospholipid compounds which may be represented by the following general formula:

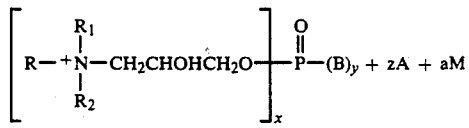

wherein:
x = 1 to 3 or mixtures thereof;
x + y = 3;
z = x;
a = 0 to 2;
B = O⁻, OM;
A = Anion;
M is a cation;

R, $R_1$ and $R_2$ are the same or different and are alkyl, substituted alkyl, alkyl aryl or alkenyl groups of up to 16 carbon atoms with the proviso that the total carbon atoms in $R+R_1+R_2$ is between 10 and 24.

The antimicrobial/virucidal phospholipid compounds described which, as indicated, exhibit broad spectrum antimicrobial as well as potent virucidal activity while being substantially non-irritating to humans, can be prepared by reaction of tertiary amines and phosphate esters corresponding to the amine and phosphate ester moieties in the above formula. Such compounds can be prepared by reacting the corresponding tertiary amine and phosphate ester reactants in the molar ratio of 1:1 to 3:1, and preferably from about 2.0:1 to 2.5:1, of amine to phosphate ester, for the time necessary for the amine to be completely reacted.

Tertiary amines suitable for use in accordance with the practice of the invention can be represented by the general formula:

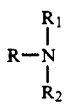

wherein R, $R_1$ and $R_2$ are the same or different and are alkyl, substituted alkyl, alkyl aryl, or alkenyl groups of up to 16 carbon atoms with the proviso that the total carbon atoms in $R+R_1+R_2$ is between 10 and 24.

Exemplary tertiary amines include:
tributylamine
(di(hydroxyethyl)hexyl)-amine
bis(2-hydroxyethyl)cocoamine
N,N-dimethyl-dodecylamine
N,N-dimethyl-tetradecylamine
N,N-dimethyl-hexadecylamine
N,N-dimethyl-cocoamine
N,N-dimethyl-cetylamine
dimethyl ($C_8$–$C_{16}$) alkyl amine The phosphate ester reactants suitable for use in accordance with the practice of the invention can be represented by the general formula:

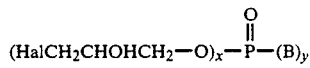

wherein:
x = 1 to 3 or mixtures thereof;
x + y = 3;
B = $O^-$ or OM;
Hal = halogen.

The phosphate ester intermediate may be prepared by known procedures wherein phosphoric acid and various phosphate salts, and preferably monosodium phosphate, are reacted in an aqueous medium with epichlorohydrin, generally in the molar ratio of from 1:1 to about 1:3, until the reaction is complete.

As noted, the instant invention is based upon the discovery that the phospholipid compounds of the invention described above are effective in controlling the growth of bacteria, yeasts and molds in diverse formulations and applications such as cosmetic, toiletries, personal care, household and related products and materials. The phospholipid agents of the invention are not only effective antimicrobials for the destruction or control of fungi and bacteria that cause degradation and deterioration of diverse personal care and household product formulations, but also by their activity against the organisms that can reside and accumulate on various surfaces, they can provide utility in sanitizing, disinfecting and bacteriostatic applications.

The antimicrobial activity of the compounds described above has been confirmed using standard laboratory techniques, including the Minimum Inhibitory Concentration (MIC) technique. They have been found effective, for example, in inhibiting bacteria including *S. aureus, E. coli, P. aeruginosa* and *S. choleraesuis*. They have also been found effective against yeast and mold including *C. albicans* and *A. niger*. In these tests it has been determined that the presence of anionic, nonionic, amphoteric and/or cationic materials did not inhibit the antimicrobial efficacy nor did a variety of inactivators commonly encountered in personal care and household applications. The broad spectrum preservative characteristics of the antimicrobial phospholipids of the invention in typical cosmetic formulations have also been established and confirmed.

Specifically, molds and yeasts which may be inhibited include *Aspergillus niger, Candida albicans* plus various species of Penicillium, Tricholphyton, Alternaria, Gliocladium, Paecilomyces, Mucor, Fusarium, Geotrichum, Cladosporium and Trichoderma. Examples of the bacteria include *Salmonella choleraesuis, Serratia marcescens, Klebsiella pneumoniae, Enterobacter aerogenes, Aerobacter aerogenes, Proteus vulgaris, Streptococcus faecalis, Pseudomonas aeruginosa, Escherichia coli, Staphylococcus aureus, Staphylococcus epidermidis, M. luteus, P. mirabilis, P. cepacia, P. stutzeri* and *A. hydrophilia*.

Another aspect of the present invention is the discovery that the antimicrobial phospholipid compounds surprisingly and unexpectedly exhibit significant spermicidal and antiviral activity which further enhances the utility of the compounds of the invention for a diversity of applications.

The virucidal activity of the phospholipid compounds described above has been confirmed using test methodology according to U.S. Environmental Protection Agency guidelines for determining the virucidal efficacy of disinfectants intended for use on dry inanimate environmental surfaces (U.S. E.P.A. Pesticide Assessment Guideline, subdivision G, Product Performance, 198, Section 91-30 pp 72-76).

Specifically, virucidal efficacy has been found against Human Influenza A virus; Herpes Simplex, type 2, virus; and the Human Immunodeficiency Virus (HIV).

The phospholipid compounds described above have activity against bacteria, yeasts, molds as well as a variety of infectious viral organisms when employed at appropriate levels of concentration and may be used to inhibit growth or effectively destroy these organisms. It should be obvious that the required effective concentration or amount will vary with particular organisms and also on a number of other factors in particular applications. In general, however, effective antimicrobial response is obtained when the active agent is employed in concentrations ranging between five and 10,000 ppm (parts per million) and preferably between about 50 and 1,000 ppm. Generally, the concentration of the agent required for bactericidal activity will be lower than the concentration required for fungicidal activity and the concentration of the agent required for virucidal activity will generally be the same or higher than the concentration required for fungicida activity.

For other applications, amounts of from 0.04% to about 5%, or higher, and preferably 0.07% to 3.0%, by weight of the active agent of the present invention is incorporated into a composition or sprayed onto or otherwise applied to a substrate to be treated in order to prevent growth of bacteria, yeasts and molds or killing and/or immobilizing infectious viral organisms. It will also be understood that the antimicrobial agents of the invention may be used in combination with other antimicrobial and/or virucidal materials.

The compatibility of the phospholipid compounds of the invention with human tissue, i.e., dermal and eye tissue has also been tested. In these tests, 48 hour human patch dermal evaluations (5% in water), in vitro ocular evaluations (3% in water) and repeated insult patch tests (3% in water) determined that the compounds are substantially non-irritating to humans, they are safe and suitable for use in eye area products and are not a skin sensitizer to humans.

While the phospholipid compounds hereinabove described exhibit broad spectrum antimicrobial as well as potent virucidal activity, certain other phospholipid compounds surprisingly have also been found to possess potent virucidal activity. Such compounds are compatible with anionic, nonionic, amphoteric and/or cationic materials without inhibition of their virucidal efficacy and exhibit low sensitivity to human tissue.

Phospolipid compounds which are also suitable as a virucidal agent have the general formula:

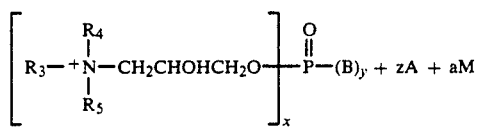

wherein:
x is as hereinabove defined;
x+y=3;
z=x;
a=0 to 2;
B=0$^-$ or OM;
A is on Anion;
M is a Cation;
$R_3$ is an amidoamine moiety of the formula:

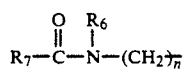

wherein:
$R_7$ is alkyl, alkenyl, alkoxy or hydroxyalkyl of from 5 to 21 carbon atoms each, or aryl or alkaryl of up to 20 carbon atoms;
$R_6$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkylene of up to 10 carbon atoms;
$R_4$ and $R_5$, which may be the same or different, are selected from alkyl, hydroxyalkyl, carboxyalkyl of up to 6 carbon atoms in each alkyl moiety, and polyoxyalkylene of up to 10 carbon atoms; in addition $R_4$ and $R_5$ taken together with the nitrogen to which they are attached may represent an N-heterocycle; and
n is an integer from 2 to 6.

The antimicrobial/virucidal phospholipid compounds of the invention may be incorporated in diverse personal care and household product formulations, as, for example, a preservative therefore and/or as a disinfectant agent, and the incorporation of the compounds of the invention into such products can be done in accordance with standard practices. The active virucidal ingredients described can be diluted or otherwise mixed with solvents, dispersants, wetting agents, carriers and the like for topical or therapeutic use as a virucide in any desired application formulation such as liquids, sprays, etc. In connection with suitable modes of application for virucidal results, the phospholipid agents can be mixed with one or more pharmaceutically acceptable solid inert carriers.

The invention will now be further illustrated by reference to certain specific examples which are provided herein for purposes of illustration only and are not intended to limit the scope therein.

Example 1

925.6 grams of soft water are charged to a reaction vessel and heat is applied to 50° C. 554.4 grams of dimethyl cocoamine ($C_{12}$—66%; $C_{14}$—26%; C16—8%) are charged into the reaction vessel under good agitation and heat is applied to 90° C. An aqueous solution of 938.8 grams of 40% active 2-propanol, 1-chlorophosphate (3:1) are charged into the reaction vessel in four equal increments over 1.5 hours using good agitation while maintaining the temperature at 90°-95° C. Heating is continued at 90°-95° C. until the pH (10%) is 6.5 or less and the percentage of free tertiary amine is 0.5% maximum; approximately six to nine hours. The reaction mixture is then cooled to 80° C., 55.2 grams of 50% NaOH are charged into the reaction vessel and the reaction mixture is heated back to 90° C. Heating at 90° C. is continued until the percentage of NaCl is 6.9±0.2 %, approximately one hour. The reaction mixture is then cooled to 50° C. and the pH (10%) is adjusted to 7.0±0.5 with citric acid (approximately 9.7 grams). 22.1 grams of $H_2O_2$ (35%) are charged to the reaction vessel with good agitation and heat is applied to 90° C. and maintained for one hour. The reaction mixture is then cooled to 50° C. and discharged. The product is a clear liquid having <0.5% free amine, a pH (10%) of 7.0±0.5 and a specific gravity @ 25° C. of 1.05.

Example 2

682.4 grams of propylene glycol and 453.0 grams of water are charged to a reaction vessel and heat is applied to 50° C. 655.2 grams of dimethyl cetylamine are charged into the reaction vessel with good agitation and heat is applied to 90° C. An aqueous solution of 938.8 grams of 40% active 2-propanol, 1 chlorophosphate (3:1) are divided into four equal increments and charged into the reaction vessel over 1.5 hours while maintaining the temperature at 90°-95° C. Heating is continued at 90°-95° C. until the pH (10%) is 6.5 or less and the free tertiary amine is <0.5%, approximately six to nine hours. The reaction mixture is then cooled to 80° C. and 47.3 grams of 50% NaOH is added with good agitation. Heat is applied to 90° C. and maintained until the percentage of NaCl is 6.1±0.2%, approximately one hour. The reaction mixture is then cooled to 50° C. and the pH (10%) is adjusted to 7.0±0.5 with citric acid, approximately 4.7 grams being added. 25 grams of 35% $H_2O_2$ are charged into the reaction vessel, heat is applied to 90° C. and maintained for one hour. The reaction mixture is then cooled to 50° C. and discharged.

The product is a clear liquid having a specific gravity @25° C. of 1.05, a pH (10%) of 7.0±0.5 and Free amine of <0.5%.

Example 3

The products of Example 1 and Example 2 are screened for antimicrobial activity using a modified Minimum Inhibitory Concentration (MIC) testing protocol. The initial screening is conducted using the following test organisms:

S. aureus ATCC #6538
C. albicans ATCC #10259
A. niger ATCC #6275
Penicillium variable ATCC #XXXX The growth media used are Brain Heart Infusion Broth for bacteria and Sabouroud Broth for yeast and mold.

A series of ten sequential two-fold dilutions of the test material is made in an appropriate growth promoting culture medium for each organism to be tested. A standard number of microorganisms are inoculated into each of the prepared dilutions containing the medium plus the test material. Inoculated tubes are incubated at appropriate temperature for 72 hours.

Visual readings are taken after 24, 48 and 72 hours. The 72-hour incubated tubes are subcultured on agar media to verify inhibition of growth. Data are recorded as positive or negative for growth at each of the dilutions of the test material under evaluation. The minimum lethal concentration is defined as the smallest concentration of antimicrobial agent that, on subculture, either fails to show growth or results in a 99.9% decrease in the initial concentration of inoculum.

Comparative MIC data of the initial screening test are reported in Table I.

TABLE I

| Test Organism | Example I Sample | Example II Sample |
|---|---|---|
| S. aureus | 20 ppm | 60 ppm |
| C. Albicans | 20 ppm | 80 ppm |
| A. niger | 10 ppm | 30 ppm |
| P. variable | 10 ppm | 80 ppm |

An additional test panel is conducted to evaluate the products of Example 1 and Example 2. The further tests are conducted with Pseudomonas aeruginosa ATCC #15442, E. coli ATCC #8739 and Salmonella choleraesuis ATCC #10708. The MIC test protocol described above is used in conducting the additional test.

Comparative MIC data of the additional screening test are reported in Table II.

TABLE II

| Test Organism | Example I | Example 2 |
|---|---|---|
| P. aerugenosa | 80 ppm | 80 ppm |
| E. coli | 20 ppm | 160 ppm |
| S. choleraesuis | 20 ppm | 80 ppm |

As can be seen, both the Example 1 and Example 2 products exhibit significant antimicrobial properties.

Example 4

A series of typical personal care products are prepared by standard practices using the following proportion of ingredients:

| Product A | Shampoo | |
|---|---|---|
| | Sodium Lauryl Sulfate | 15.0% by weight |
| | Water | 85.0% |
| | Antimicrobial Phospholipid (Example 1) | variable |

Compositions are prepared with the following proportions of the product of Example 1.

| Test Sample | Example 1 Product |
|---|---|
| A-1 | 0.00% by weight |
| A-2 | 0.25% by weight |
| A-3 | 0.50% by weight |
| A-4 | 1.00% by weight |

| Product B | Make-Up Foundation | |
|---|---|---|
| a) | Steareth - 20 | 1.5% by weight |
| | Pigment | 15.0% by weight |
| | 0.5% Kelzan AR/1% NaCl | 76.0% by weight |
| b) | Steareth - 2 | 2.5% by weight |
| | Isopropyl Myristate | 2.0% by weight |
| | Hexyl Laurate | 2.0% by weight |
| | Dow Fluid 200/100 cs | 1.0% by weight |
| | Antimicrobial Phospholipid | variable |
| | Pigment: White | 13.50% by weight |
| | Red | 0.15% by weight |
| | Brown | 1.20% by weight |
| | Yellow | 0.15% by weight |

Compositions are prepared with the following proportions of the product of Example 1.

| Test Sample | Example 1 Product |
|---|---|
| B-1 | 0.00% by weight |
| B-2 | 0.25% by weight |
| B-3 | 0.50% by weight |
| B-4 | 1.0% by weight |

| Product C | Lotion | |
|---|---|---|
| a) | Steareth - 20 | 2.0% by weight |
| | Water | 87.5% by weight |
| | Product of Example 1 | variable |
| b) | Steareth - 2 | 3.0% by weight |
| | Isopropyl Myristate | 5.0% by weight |
| | Cetearyl Alcohol | 2.5% by weight |

Compositions are prepared with the following proportions of the product of Example 1.

| Test Sample | Example 1 Product | |
|---|---|---|
| C-1 | Product of Example 1 | 0.0% by weight |
| C-2 | Product of Example 1 | 0.1% by weight |
| C-3 | Product of Example 1 | 0.5% by weight |

Example 5

The personal care products of Example 4 are subject to Preservative Challenge Tests as follows:

Aliquots of each test preparation are inoculated with separate representative mixed cultures of bacteria and fungi. Plate counts to determine survivors are performed at 0 time and after 3, 7, 14, 21 and 28 days of incubation. Bacterial samples showing a less than 10 recovery at 14 days are re-inoculated at days. Results are presented as surviving organisms present at each time interval per gram of product tested.

PRODUCT A

Inoculum a) Mixed bacteria: *Pseud. Aeruginosa* (ATCC 15442); *E. coli* (ATCC 8739 or 11229); *S. aureus* (ATCC 6536).

b) Mixed fungi: *A. niger* (ATCC 9642); *P. luteum* (ATCC 8644); *C. albicans* (ATCC 10231).

| TEST SAMPLE | DAYS | BACTERIA | FUNGI | CONTROL |
|---|---|---|---|---|
| A-1 | 0 | 2,100,000 | 740,000 | <10 |
|  | 3 | 17,500 | 4,750 | <10 |
|  | 7 | 2,100,000 | 740,000 | <10 |
|  | 14 | 2,100,000 | 740,000 | <10 |
|  | 21* | 2,100,000 | 740,000 | <10 |
|  | 28 | 2,100,000 | 740,000 | <10 |
| A-2 | 0 | 2,100,000 | 740,000 | <10 |
|  | 3 | 24,200 | 1,900 | <10 |
|  | 7 | <10 | <10 | <10 |
|  | 14 | <10 | <10 | <10 |
|  | 21* | <10 | <10 | <10 |
|  | 28 | <10 | <10 | <10 |
| A-3 | 0 | 2,100,000 | 740,000 | <10 |
|  | 3 | 16,900 | 9,700 | <10 |
|  | 7 | <10 | <10 | <10 |
|  | 14 | <10 | <10 | <10 |
|  | 21* | <10 | <10 | <10 |
|  | 28 | <10 | <10 | <10 |
| A-4 | 0 | 2,100,000 | 740,000 | <10 |
|  | 3 | 23,700 | 1,620 | <10 |
|  | 7 | <10 | <10 | <10 |
|  | 14 | <10 | <10 | <10 |
|  | 21* | <10 | <10 | <10 |
|  | 28 | <10 | <10 | <10 |

*21-day Re-inoculation
NOTE:
Control is an uninoculated sample for background count.
Bacterial and Fungal Counts are as organisms recovered per gram of sample.
Test Day is the number of days after inoculation of the test sample.

As can be seen, the antimicrobial product of Example #1 is highly effective against both bacterial and fungal challenges at a concentration of 0.25%. Moreover, the antimicrobial product of Example #1 is not adversely affected by anionics such as sodium lauryl sulfate.

PRODUCT B

Inoculum a) Mixed bacteria: *Pseud. aeruginosa* (ATCC 15442); *E. coli* (ATCC 8739 or 11229); *S. aureus* (ATCC 6536).

b) Mixed fungi: *A. niger* (ATCC 9642); *P. luteum* (ATCC 9644); *C. albicans* (ATCC 10231).

| TEST SAMPLE | DAYS | BACTERIA | FUNGI | CONTROL |
|---|---|---|---|---|
| B-1 | 0 | 2,100,000 | 740,000 | <10 |
|  | 3 | 2,100,000 | 740,000 | <10 |
|  | 7 | 2,100,000 | 740,000 | <10 |
|  | 14 | 2,100,000 | 740,000 | <10 |
|  | 21* | 2,100,000 | 740,000 | <10 |
|  | 28 | 2,100,000 | 740,000 | <10 |
| B-2 | 0 | 1,980,000 | 750,000 | <10 |
|  | 3 | 57,000 | 4,200 | <10 |
|  | 7 | <10 | 120 | <10 |
|  | 14 | <10 | 1,420 | <10 |
|  | 21* | <10 | 5,300 | <10 |
|  | 28 | <10 | 7,400 | <10 |
| B-3 | 0 | 2,100,000 | 740,000 | <10 |
|  | 3 | 12,000 | 3,400 | <10 |
|  | 7 | <10 | <10 | <10 |
|  | 14 | <10 | <10 | <10 |
|  | 21* | <10 | <10 | <10 |
|  | 28 | <10 | <10 | <10 |
| B-4 | 0 | 2,100,000 | 700,000 | <10 |
|  | 3 | 3,000 | <10 | <10 |
|  | 7 | <10 | <10 | <10 |
|  | 14 | <10 | <10 | <10 |
|  | 21* | <10 | <10 | <10 |
|  | 28 | <10 | <10 | <10 |

*21-day Re-inoculation
NOTE:
Control is an uninoculated sample for background count.
Bacterial and Fungal Counts are as organisms recovered per gram of sample.
Test Day is the number of days after inoculation of the test sample.

As can be seen, the antimicrobial product of Example #1 is highly effective against both bacterial and fungal challenges at a concentration of 0.50%. At 0.25%, the product of Example #1 is effective against the bacterial inoculum but failed to completely eradicate the fungi after initial reductions were noted.

PRODUCT C

Inoculum a) Mixed bacteria: *Pseud. aeruginosa* (ATCC 15442); *E. coli* (ATCC 8739 or 11229); *S. aureus* (ATCC 6536).

b) Mixed fungi: *A. niger* (ATCC 9642); *P. luteum* (ATCC 9644); *C. albicans* (ATCC 10231).

| TEST SAMPLE | DAYS | BACTERIA | FUNGI | CONTROL (Uninoculated) |
|---|---|---|---|---|
| C-1 | 0 | 2,100,000 | 310,000 | 610 |
|  | 3 | 2,700,000 | 350,000 | 1,220 |
|  | 7 | TNTC* | TNTC | TNTC |
|  | 14 | TNTC | TNTC | TNTC |
|  | 21 | TNTC | TNTC | TNTC |
|  | 28 | TNTC | TNTC | TNTC |
| C-2 | 0 | 2,400,000 | 250,000 | <10 |
|  | 3 | <10 | 6,340 | <10 |
|  | 7 | <10 | 5,100 | <10 |
|  | 14 | <10 | 1,260 | <10 |
|  | 21* | <10 | 2,140 | <10 |
|  | 28 | <10 | 2,970 | <10 |
| C-3 | 0 | 1,900,000 | 290,000 | <10 |
|  | 3 | <10 | 2,170 | <10 |
|  | 7 | <10 | <10 | <10 |
|  | 14 | <10 | <10 | <10 |
|  | 21* | <10 | <10 | <10 |
|  | 28 | <10 | <10 | <10 |

*TNTC - Too numerous to Count
*21-day Re-inoculation
NOTE:
Control is an uninoculated sample for background count.
Bacterial and Fungal Counts are as organisms recovered per gram of sample.
Test Day is the number of days after inoculation of the test sample.

As can be seen, Test sample C-3 (0.5% Product of Example #1) is found to effectively eliminate both bacterial and fungal challenges within seven days of inoculation. The product of Example #1 at 0.5% is capable of functioning effectively as a preservative as measured by the above test parameters.

The antimicrobial test results clearly show the effectiveness of these products in preserving these systems. Noteworthy is the fact that product of Example #1 is not affected by anionics such as sodium lauryl sulfate.

Example 6

The virucidal efficacy of the product of Example 1 against human influenza A virus is demonstrated in this example.

In this test, virucidal efficacy of the test sample is evaluated by reduction in infectivity recoverable from a virus-contaminated surface after exposure to the use-dilution of the product. The test is conducted according to U.S. Environmental Protection Agency guidelines for determining the virucidal efficacy of disinfectants intended for use on dry inanimate surfaces (U.S.E.P.A. Pesticide Assessment Guidelines, Subdivision G: Product Performance, 1982, Section 91-30, pp. 72-76). In order for disinfectant efficacy to be claimed, the following criteria must be met in the test:

1. At least four logs of virus infectivity must be demonstrated, i.e. it must be possible to dilute the virus control four times 10-fold serially and still be able to detect infectious virus in the $10^{-4}$ dilution.

2. The disinfectant must cause a 3 log reduction in virus titer.

3. There can be no detectable virus in the lowest non-toxic dilution of the virus-disinfectant sample.

Human influenza A, strain A2/Hong Kong/8/68, ATCC VR-544, is the virus used in the study of this example. The virus suspension is prepared in allantoic fluid.

The phospholipid compound used in this example is diluted for evaluation on the day of use 1:40 in sterile deionized water.

Fertile chicken eggs incubated at 37 degrees C. are used which are candled on the day of inoculation; only live embryonated eggs being used. The embryonated eggs are inoculated after 10 days of incubation.

The films of virus are made by placing 0.2 ml amounts of undiluted virus suspension on the bottoms of sterile glass Petri dishes and spreading. Films are held at room temperature (approx. 23 degrees C.) and ambient humidity, protected from direct light until dry (approximately 35 minutes).

The dried virus films are treated with 2.0 ml of the use-dilution of the disinfectant sample for an exposure period of 10 minutes at approximately 23 degrees C. After exposure, the bottom of the dish is scraped with a rubber policeman to remove the virus disinfectant mixture.

Concurrently with disinfectant treatment of one virus film, a parallel virus control film is resuspended in 1 ml of Phosphate-buffered saline (PBS).

Assays for virus recovery are carried out by immediately making serial dilutions in PBS with the virus-disinfectant and virus control preparations and subsequently inoculating into embryonated eggs At least four (4) eggs are used per dilution. The eggs are inoculated with 0.2 ml volumes, and incubated at 37 degrees C. for approximately 72 hours with daily examination for mortality, and then cooled overnight at 4 to 6 degrees C. Allantoic fluids are collected from each egg and centrifuged for 10 minutes at approximately 800 xx g. Hemagglutination (HA) tests are carried out by mixing 0.5 ml of each fluid with 0.5 ml of 0.5% chicken erythrocytes (in PBS and observing for HA during the next one to two hours at room temperature.

Cytotoxicity controls are run by diluting the use-dilution of the lot of disinfectant sample serially in PBS, and inoculating into embryonated eggs concurrently with virus-disinfectant mixtures. The viability of embryonated eggs is determined daily for three days of incubation at 37 degrees C.

Viral and cytotoxicity titers are reported as $-\log_{10}$ of the 50% titration endpoint for infectivity ($ID_{50}$) or toxicity ($TD_{50}$), as calculated by the method of Reed and Miuench (Amer. J. Hyg. 27: 493-497, 1938).

Results of the study are reported in Table III.

TABLE III

HUMAN INFLUENZA A VIRUS
Evaluation of the PHOSPHOLIPID Sample for virucidal efficacy against dried virus after a 10-minute exposure to a 1:40 dilution in sterile deionized water.

| Dilution Inoculated | Control | Hemagglutination (HA) (No. Positive/ Inoculated) Sample + Virus | Cytotoxicity Controls (No. Dead/No. Inoculated) |
|---|---|---|---|
| $10^{-1}$ | 4/4 | 0/4 | 0/4 |
| $10^{-2}$ | 4/4 | 0/4 | 0/4 |
| $10^{-3}$ | 4/4 | 0/4 | 0/4 |
| $10^{-4}$ | 2/4 | 0/4 | 0/4 |
| Virus Titer ($-\log_{10}$) $ID_{50}$) HA Assay | 4/0 | ≦0.5 | |
| Cytotoxicity Titer ($-\log_{10}$ $TD_{50}$)– | | | ≧0.5 |
| Reduction of virus titer by test sample ($-\log_{10}$ $ID5_0$)– HA Assay | | ≧3.5 | |

Based on the results of infectivity and cytotoxicity assays shown in Table III, the Phospholipid example demonstrates virucidal activity against human influenza A. Infectivity is not detected in the virus-disinfectant mixture at the lowest nontoxic dilution. The reduction in virus titer for the phospholipid product of Example 1 is ≧3.5 log.

Example 7

The virucidal efficacy of the product of Example 1 against Herpes Simplex, Type 2 is demonstrated in this example.

The virucidal efficacy assay of this example generally employs the assay method of Example 6 except as noted. The virus employed is Herpes Simplex, type 2, ATCC VR-734 prepared in tissue culture medium. The cell cultures used are prepared from Vero cells obtained from Southern Research Institute with the cultures routinely grown in supplemented minimal essential medium (MEM). The cultures are grown and used as monolayers in disposable tissue culture labware at 37 degrees C in a humidified atmosphere of 5% $CO_2$ in air. After infection, cultures are held in maintenance medium containing the same ingredients with a 2% fetal calf serum.

The reagents, disinfectant test solution and preparation of virus films are as described in Example 6.

Treatment of Virus Films with Disinfectant: —Dried virus films are treated with 2.0 ml of the use-dilution of the disinfectant sample and allowed to remain in contact for a total exposure period of ten minutes at approximately 23 degrees C. After approximately the first 6.5 minutes of exposure, the bottom of the dish is scraped with a rubber policeman, and an aliquot of the virus-disinfectant mixture is immediately added to a Sephadex column for separation of virus from disinfectant by gel filtration. Concurrently with disinfectant treatment of one virus film, a parallel virus control film is resuspended in 2 ml of Phosphate buffered saline (PBS) and an aliquot is applied to a Sephadex column after 6.5 minutes. Sephadex gel filtration is performed generally by the method of Blackwell and Chen (J.AOAC 53: 1229-1236, 1970). The column filtrates are collected and diluted ten-fold serially for assay of infectivity.

Assays for virus recovery are made using dilutions of each virus-disinfectant and control virus preparation. The dilutions are inoculated into cell cultures, at least four cultures per dilution being used. Cell monolayers are inoculated with 0.05 ml and incubated for one hour at 37 degrees C. After absorption, maintenance medium (0.2 ml) is added and cultures are incubated at 37 degrees C. Cultures are scored for cytopathic effects (CPE) at seven days after inoculation.

Cytotoxicity controls of each batch of disinfectant sample are determined by placing 2.0 ml in the bottom of a sterile Petri dish containing a film of 0.2 ml PBS and after about 6.5 minutes an aliquot is filtered through Sephadex. The column filtrates are collected and diluted ten-fold serially for titration of cytotoxicity.

Calculations of results are carried out as described in Example 6.

The results of infectivity and cytotoxicity assays are reported in Table IV.

TABLE IV

| Dilution Inoculated | Cytopathic-Cytotoxic Effects (No. Positive/ No. Inoculated) | | Cytotoxicity Controls |
|---|---|---|---|
| | Control | Sample + Virus | |
| $10^{-1}$ | 4/4 | 0/4 | 0/4 |
| $10^{-2}$ | 4/4 | 0/4 | 0/4 |
| $10^{-3}$ | 4/4 | 0/4 | 0/4 |
| $10^{-4}$ | 2/4 | 0/4 | 0/4 |
| Virus Titer ($-\log_{10}$) $ID_{50}$) | 4.0 | $\leq 0.5$ | |
| Cytotoxicity Titer ($-\log_{10} TD_{50}$)— | | | $\geq 0.5$ |
| Reduction of virus titer by test sample ($-\log_{10} ID_50$)— | | $\geq 3.5$ | |

Example 8

In this example, the virucidal efficacy of the product of Example 1 is evaluated as measured by the reduction in infectivity of Human Immunodeficiency Virus, HTLF-III$_{RF}$ strain of HIV-1 using test protocols as described in Example 7.

Preparation of the Starting Materials

The RF Strain of HTLV-III human immunodeficiency virus (HIV) is used in this study. The Virus is produced by cultures of RF virus-infected H$_9$ cells (H9/RF) and is concentrated from supernatant culture fluid by high speed centrifugation by the following procedure: cells are first pelleted from a H9/RF culture by centrifugation at 600× g for 15 minutes at 4 degrees C. The supernatant culture fluid is transferred to 50 ml centrifuge tubes and centrifuged at 32,500× g. for 90 minutes at 4 degrees C. The supernatant is decanted and the virus pellet is resuspended in 1/100 the original volume of complete RPMI 1640 medium without fetal bovine serum. Resuspended virus pellets are kept at 4 degrees C. until used to prepare virus films.

The disinfectant used in this example is diluted 1:40 on the day of use in sterile deionized water.

Phosphate-buffered saline (PBS) is that of Dulbecco and Vogt, 1954.

Films of virus are made by spreading 0.2 ml amounts of concentrated virus suspension over 28 cm$^2$ on the bottom of sterile glass Petri dishes. Films are held at room temperature (approx. 23 degrees C.) until visibly dry (approximately 45 minutes) and then incubated at 35–37 degrees C. in a dry oven for an additional 30 minutes to increase the level of dryness.

Method of Determining Virucidal Efficacy of Disinfectant

Treatment of Virus Films with Disinfectant: Dried virus films are treated with 2 ml of the diluted disinfectant and allowed to remain in contact for a total exposure period of 10 minutes at approximately 23 degrees C. After about 6.5 minutes of exposure, the treated virus films are filtered in a Sephadex column as described in Example 7. The column filtrates are diluted 10-fold for assay of infectivity.

Treatment of Virus Control Films: A parallel virus film is resuspended in 2 ml of RPM 1640 medium without fetal bovine serum and antibiotics. After Sephadex filtration, the column filtrate is diluted 10-fold serially for assay of infectivity.

Cytotoxicity Controls: The cytotoxicity of each batch of disinfectant test sample is prepared by placing 2 ml of the diluted disinfectant test sample in the bottom of a sterile Petri dish containing a film of dried PBS (0.2 ml). After about the first 6.5 minutes, an aliquot is filtered through Sephadex and subsequently diluted 10-fold serially for assay of cytotoxicity.

Infectivity Assay: MT2 cells are indicator cells for infectivity assay. The MT2 cells are treated with polybrene (2 μg/ml) for 30 minutes at 37 degrees C., collected by centrifugation and plated in 96-well culture plates at approximately 1×10$^4$ cells per well in 0.15 ml of medium. Dilutions of each of the test and control groups are inoculated (0.05 ml/well) into four replicate cultures of MT2 cells and the cultures are scored for lytic cytopathic effects (CPE) after eight days of incubation at 37 degrees C. Viral and cyctotoxicity titers are expressed in this example as $-\log_{10}$ of the 50 percent titration endpoint for infectivity (ID$_{50}$) or toxicity (TD$_{50}$), respectively, as calculated by the method of Reed and Muench.

The results of infectivity and cytotoxicity assays are shown in Table V.

TABLE V

| Dilution Inoculate | CPE Assay with MT2 Cells (Day 8) Cytopathic-Cytotoxic Effects (No. Positive/No. Inoculated) | | Cytotoxicity Controls |
|---|---|---|---|
| | Control | Sample + Virus | |
| $10^{-1}$ | | Toxic | 0/4 |
| $10^{-2}$ | 4/4 | 0/4 | 0/4 |
| $10^{-3}$ | 4/4 | 0/4 | 0/4 |
| $10^{-4}$ | 0/4 | 0/4 | 0/4 |
| Virus Titer ($-\log_{10}$) ID$_{50}$) | 5.7 | $\leq 1.5$ | |
| Cytotoxicity Titer ($-\log_{10} TD_{50}$)— | | | $\geq 0.5$ |
| Reduction of virus titer by test sample ($-\log_{10} ID_{50}$)— | | $\leq 4.2$ | |

The results of infectivity and cytotoxicity demonstrated that the product of Example 1 possessed virucidal activity against HIV-1 in a CPE assay with MT2 cells.

Example 9

The virucidal efficacy of various synthetic phospholipid compounds against human influenza A virus is demonstrated in this example.

The synthetic phospholipid compounds evaluated in this example are:

Product A—Cocamidopropyl PG—Dimonium Chloride Phosphate available commercially under the tradename PHOSPHOLIPID PTC from Mona Industries.

Product B—Stearamidopropyl PG—Dimonium Chloride Phosphate available commercially under the tradename PHOSPHOLIPID SV from Mona Industries.

In this Example, virucidal efficacy of Product A and Product B are evaluated by reduction in infectivity recoverable from a virus-contaminated surface after exposure to the use-dilution of the test products. The tests are conducted according to U.S. Environmental Protection Agency guidelines described in Example 6.

Human influenza A virus, strain A/PR/834, ATCC VR-95 is used in the studies of this example. The virus suspension is prepared in tissue culture medium and is held in maintenance medium after infection containing the same ingredients in which the cultures are routinely grown but with 2% fetal calf serum instead of 10% serum.

Virus films to be used are prepared as described in Example 6 as are the disinfectant product samples and phosphate-buffered saline (PBS) reagent.

Treatment of virus films with disinfectant is carried out by treating dried virus films with 2.0 ml of the use-dilution of the disinfectant test samples and allowed to remain in contact for a total exposure period of 10 minutes at approximately 23 degrees C. After about the first 6.5 minutes of exposure, the bottom of the Petri dish is scraped with a rubber policeman, and an aliquot of the virus-disinfectant mixture is immediately added to a Sephadex column for separation of virus from disinfectant by gel filtration (see Example 7).

Concurrently with disinfectant treatment of one virus film, a parallel virus control film is resuspended in 2 ml of PBS and an aliquot is applied to a Sephadex column after 6.5 minutes.

The assays for virus recovery are carried out by making dilutions of each virus-disinfectant and control virus preparation and inoculating then into cell cultures. At least four cultures are used per dilution. Cell monolayers are inoculated with 0.05 ml and incubated for one hour at 37 degrees C. After absorption, maintenance medium (0.2 ml) is added and cultures are incubated at 37 degrees C. The cultures are scored for cytopathic effects (CPE) at seven days after inoculation.

The cytotoxicity of each batch of disinfectant test sample is determined by placing 2.0 ml in the bottom of a sterile Petri dish containing a film of 0.2 ml PBS. After approximately 6.5 minutes, an aliquot is filtered through Sephadex. The column filtrates are collected and diluted 10-fold serially for titration of cytotoxicity.

Viral and cytotoxicity titers are expressed as described in Example 7 and 8.

The results of infectivity and cytotoxicity assays are shown in Table VI for both Product A and Product B.

TABLE VI

HUMAN INFLUENZA A VIRUS
Evaluation of PRODUCT A AND PRODUCT B for virucidal efficacy
against dried virus after a 10-minute exposure
to a 1:40 dilution in sterile deionized water

| Dilution Inoculated | Virus Control | (No. Positive/ No. Inoculated) Sample + Virus | | No. Dead/ No. Inoculated) Cytotoxicity Controls | |
|---|---|---|---|---|---|
| | | PRODUCT A | PRODUCT B | PRODUCT A | PRODUCT B |
| $10^{-1}$ | 4/4 | Toxic | Toxic | 4/4 | 4/4 |
| $10^{-2}$ | 4/4 | Toxic | Toxic | 4/4 | 4/4 |
| $10^{-3}$ | 4/4 | Toxic | Toxic | 4/4 | 4/4 |
| $10^{-4}$ | 2/4 | 0/4 | 0/4 | 0/4 | 0/4 |
| Virus Titer ($-\log_{10}$) $TCID_{50}$) | 5.7 | $\leq 3.5$ | $\leq 3.5$ | | |
| Cytotoxicity ($-\log_{10} TCTD_{50}$) | | | 3.5 | 3.5 | 3.5 |
| Reduction of virus titer by test sample ($-\log_{10} TCID_{50}$) | | $\geq 2.2$ | $\geq 2.2$ | | |

The results of infectivity and cytotoxicity demonstrate that Product A and Product B possess virucidal activity against human influenza A virus.

Example 10

The virucidal efficacy of Product A and Product B of Example 9 against Herpes Simplex, Type 2 virus is demonstrated in this example.

The procedure and ingredients of Example 7 are used in this study of the virucidal efficacy against Herpes Symplex Type 2, ATCC VR-734.

The results of infectivity and cytotoxicity assays are shown in Table VII.

TABLE VII

HERPES SIMPLEX, TYPE 2
Evaluation of PRODUCT A AND PRODUCT B for virucidal efficacy
against dried virus after a 10-minute exposure
to a 1:40 dilution in sterile deionized water
Cytopathic-Cytotoxic Effects
(No. Positive/No. Inoculated)

| Dilution Inoculated | Virus Control | Sample + Virus | | Cytotoxicity Controls | |
|---|---|---|---|---|---|
| | | PRODUCT A | PRODUCT B | PRODUCT A | PRODUCT B |
| $10^{-1}$ | 4/4 | Toxic | Toxic | 4/4 | 4/4 |

TABLE VII-continued
HERPES SIMPLEX, TYPE 2
Evaluation of PRODUCT A AND PRODUCT B for virucidal efficacy
against dried virus after a 10-minute exposure
to a 1:40 dilution in sterile deionized water
Cytopathic-Cytotoxic Effects
(No. Positive/No. Inoculated)

| Dilution Inoculated | Virus Control | Sample + Virus | | Cytotoxicity Controls | |
|---|---|---|---|---|---|
| | | PRODUCT A | PRODUCT B | PRODUCT A | PRODUCT B |
| $10^{-2}$ | 4/4 | Toxic | Toxic | 4/4 | 4/4 |
| $10^{-3}$ | 4/4 | 0/4 | 0/4 | 0/4 | 0/4 |
| $10^{-4}$ | 2/4 | 0/4 | 0/4 | 0/4 | 0/4 |
| Virus Titer ($-\log_{10}$) $TCID_{50}$) | 5.5 | $\leq 2.5$ | $\leq 2.5$ | | |
| Cytotoxicity ($-\log_{10} TCTD_{50}$) | | | | 2.5 | 2.5 |
| Reduction of virus titer by test sample ($-\log_{10} TCID_{50}$) | | $\geq 3.0$ | $\geq 3.0$ | | |

Having now fully described the invention, it will be apparent to one of ordinary skill in the art that many changes and modifications can be made thereto without departing from the spirit or scope of invention as set forth herein.

What is claimed is:

1. A method of providing virucidal activity to a substrate surface subject to contact by infections viral organisms which comprises treating a substrate surface subject to contact by infectious viral organisms with a virucidally effective amount of a composition selected from a synthetic from a synthetic phospholipid of the formula:

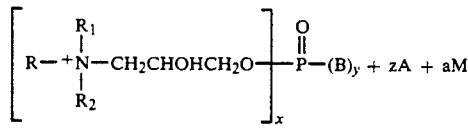

wherein:
x = 1 to 3 or mixtures thereof;
x + y = 3;
z = x;
a = 0 to 2;
B = O⁻ or OM;
A = Anion;
M is a cation;
R, $R_1$ and $R_2$ are the same or different and are alkyl, substituted alkyl, alkyl aryl or alkenyl groups of up to 16 carbon atoms with the proviso that the total carbon atoms in R + $R_1$ + $R_2$ is between 10 and 24;

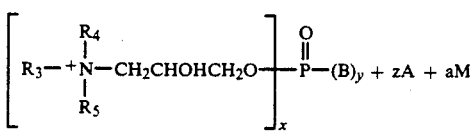

wherein:
x is as hereinabove defined;
x + y = 3;
z = x;
a = 0 to 2;
B = O⁻ or OM;
A is on Anion;
M is a Cation;
$R_3$ is an amidoamine moiety of the formula:

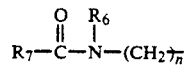

wherein:
$R_7$ is alkyl, alkenyl, alkoxy or hydroxyalkyl of from 5 to 21 carbon atoms each, or aryl or alkaryl of up to 20 carbon atoms;
$R_6$ is hydrogen or alkyl, hydroxyalkyl or alkenyl of up to 6 carbon atoms each or cycloalkyl of up to 6 carbon atoms, polyoxyalkylene of up to 10 carbon atoms;
$R_4$ and $R_5$, may be the same or different, are selected from alkyl, hydroxyalkyl, carboxyalkyl of up to 6 carbon atoms in each alkyl moiety, and polyoxyalkylene of up to 10 carbon atoms; in addition $R_4$ and $R_5$ taken together with the nitrogen to which they are attached may represent an N-heterocycle; and
n is an integer from about 2 to 6;
or mixtures thereof.

2. The method of providing virucidal activity to a substrate surface according to claim 1, wherein said composition is a synthetic phospholipid of the formula:

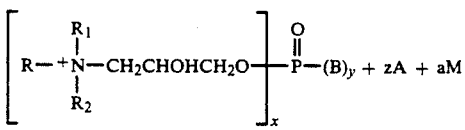

wherein:
x = 1 to 3 or mixtures thereof;
x + y = 3;
z = x;
a = 0 to 2;
B = O⁻ or OM;
A = Anion;
M is a cation;
R, $R_1$ and $R_2$ are the same or different and are alkyl, substituted alkyl, alkyl aryl or alkenyl groups of up to 16 carbon atoms with the proviso that the total carbon atoms in $R+R_1+R_2$ is between 10 and 24.

3. A method of providing virucidal activity to a substrate surface subject to contact by infectious viral organisms which comprises treating a substrate subject to contact by infectious viral organisms with a virucidally effective amount of a virucidal agent comprising a phospholipid of the formula:

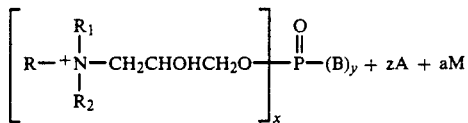

wherein:
x = 1 to 3 or mixtures thereof;
x + y = 3;
z = x;
a = 0 to 2;
B = O$^-$ or OM;
A = Anion;
M is a cation;
R, $R_1$ and $R_2$ are the same or different and are alkyl, substituted alkyl, alkyl aryl or alkenyl groups of up to 16 carbon atoms with the proviso that the total carbon atoms in $R+R_1+R_2$ is between 10 and 24.

* * * * *